United States Patent [19]

Knutsson et al.

[11] Patent Number: 5,313,956
[45] Date of Patent: May 24, 1994

[54] APPARATUS FOR MEASURING THE TRANSPORT TIME OF NERVE SIGNALS

[75] Inventors: Evert Knutsson; Lennart Gransberg, both of Djursholm, Sweden

[73] Assignee: Dorsograf AB, Malmo, Sweden

[21] Appl. No.: 915,994

[22] PCT Filed: Dec. 3, 1991

[86] PCT No.: PCT/SE91/00822
§ 371 Date: Aug. 4, 1992
§ 102(e) Date: Aug. 4, 1992

[87] PCT Pub. No.: WO92/10134
PCT Pub. Date: Jun. 25, 1992

[30] Foreign Application Priority Data

Dec. 4, 1990 [SE] Sweden .................. 9003853-0

[51] Int. Cl.5 ............................ A61B 5/05
[52] U.S. Cl. ..................... 128/741; 128/732
[58] Field of Search ........... 128/732, 741, 734, 783, 128/795, 797, 905

[56] References Cited

U.S. PATENT DOCUMENTS

| 3,650,264 | 3/1972 | Janssen | 128/2.06 A |
| 4,064,870 | 12/1977 | Dumitrescu et al. | 128/2 N |
| 4,170,225 | 10/1979 | Criglar et al. | 128/732 |
| 4,570,640 | 2/1986 | Barsa | 128/741 |
| 4,794,934 | 1/1989 | Motoyama et al. | 128/734 |
| 4,807,643 | 2/1989 | Rosier | 128/741 |

Primary Examiner—Max Hindenburg
Attorney, Agent, or Firm—Fisher, Christen & Sabol

[57] ABSTRACT

The invention relates to apparatus which includes stimulating electrodes (2,3) through which electrical signals are applied to an extremity of a patient (1). Detecting electrodes (30,40) are disposed along the patient's spine and on the crown of the patient' head. The apparatus also includes signal amplifiers (7,8), a loudspeaker (9) or the like to which an amplified signal is applied for physiological feedback purposes, an A/D-converter and a computer (20). Samples of signals are collected so as to obtain from the distributed electrodes means value curves from which the transport time of the nerve signals from respective extremities can be determined.

20 Claims, 3 Drawing Sheets

APPARATUS FOR MEASURING THE TRANSPORT TIME OF NERVE SIGNALS

FIELD OF THE INVENTION

The present invention relates to an apparatus for measuring the transport time of nerve signals.

BACKGROUND OF THE INVENTION

Apparatus are known and used for diagnosing certain types of nerve damage. For example, it is usual to apply electrical stimulating pulses to a heel of a patient with the patient lying flat on his stomach, and to measure the arrival time at the brain cortex, by attaching two electrodes to the skin of the crown of the patient's head, wherewith in the case of a normal person a signal of the order of 0.5-3 $\mu$V will occur between the electrodes after a time lapse of 39.5±3.3 ms from the time of administering the stimulating pulses. Although this signal contains a fair amount of noise, it is possible to obtain a summation signal from which the transport time can be determined with the aid of graphic methods or the like, by adding together a large number of signals.

Endeavours have also been made to obtain a more complete picture of the transport of the nerve signals, by positioning detectors along the spine, for instance so as to ascertain whether or not the function is influenced by defects in the spinal column. In this case, however, the disturbances which emanate from the muscles and the heart are much more troublesome. In order to eliminate these disturbances, incisive methods have been attempted, in which electrodes are inserted into the vertebral canal. Endeavours to measure the transport time of nerve signals have also been made with a combination of long measuring periods and patient relax periods, in which the patient is put to sleep or medicated. These investigations, however, cannot be carried out in polyclinics and are expensive, time consuming and somewhat unpleasant for the patient.

SUMMARY OF THE INVENTION

The object of the invention is to provide apparatus which will enable measurements of this kind to be carried out and which will also enable the transport time of nerve impulses from an extremity of the patient to the cortex to be mapped within a short period of time with the patient normally awake, so as to enable the investigation to be carried out in polyclinic facilities. There is a great need for investigations such as these, particularly in the case of patients suffering from back trouble and back pains, where it is known at present that if the patient is put on the sick list and does not return to normal or rehabilitates within three months, the patient will become permanently unfit for work, in up to 90% of the cases involved. A quick diagnosis carried out in a polyclinic within a short space of time is able to save the majority of these people and to return them to a normal life, by treating the patients adequately in time.

The most important problem solved by means of the present invention pertains to the signal to noise ratio in its widest meaning. Firstly, the signals are very small and are therefore subjected to normal noise. Secondly, artifacts exist, i.e. disturbances in the form of muscle impulses for instance, EMG, which can reach up to ±500 $\mu$V, and impulses deriving from cardiac activity, ECG, which can reach up to ±2000 $\mu$V, which shall be compared with the useful signals having an order of magnitude of only some $\mu$V.

These problems are far less troublesome when the signals are detected with the aid of electrodes placed on the crown of the patient's head, since only smaller artifacts are caused by the spontaneous activity of the cerebral cortex, EG, and to some extent by eye movements.

According to the present invention, in addition to the electrodes placed on the patient's crown, electrodes can also be placed along the patient's spine so as to record simultaneously response curves at different locations, e.g. from 4 to 9 or more spinal locations.

The aforesaid problem is solved in accordance with the invention through a combination of two different features, namely by reducing the "muscle signals" as a result of making such signals audible to the patient through a loudspeaker (or through earphones or by visibilizing said signals), so that the patient himself is able to reduce these signals and relax through an adaptive feedback, and by an effective weeding of the signals with the aid of an appropriate algorithm so that only those signal sequences which appear to be relatively undisturbed are recorded and summated to provide mean curves.

Another difficulty is encountered when wishing to make a comparitive investigation between the left and the right side of a patient. In conventional methods, first the one side is investigated and then the other. The result is often unreliable, because of variations in excitability within the central nervous system.

Consequently, in accordance with one preferred embodiment of the invention, two sets of stimulating electrodes are attached to respective extremities, generally to the patient's heels, and activated alternately, the storage and processing of the resultant signals being effected in separate memory stores. It is suitable to activate the right extremity each alternate time and to activate the left extremity at times therebetween. In many cases, it may be suitable to attach one set of electrodes to a leg of the patient and the other set to an arm.

The invention will now be described in more detail on the basis of a non-limiting exemplifying embodiment thereof.

DESCRIPTION OF THE PREFERRED EMBODIMENTS

Figure 1:
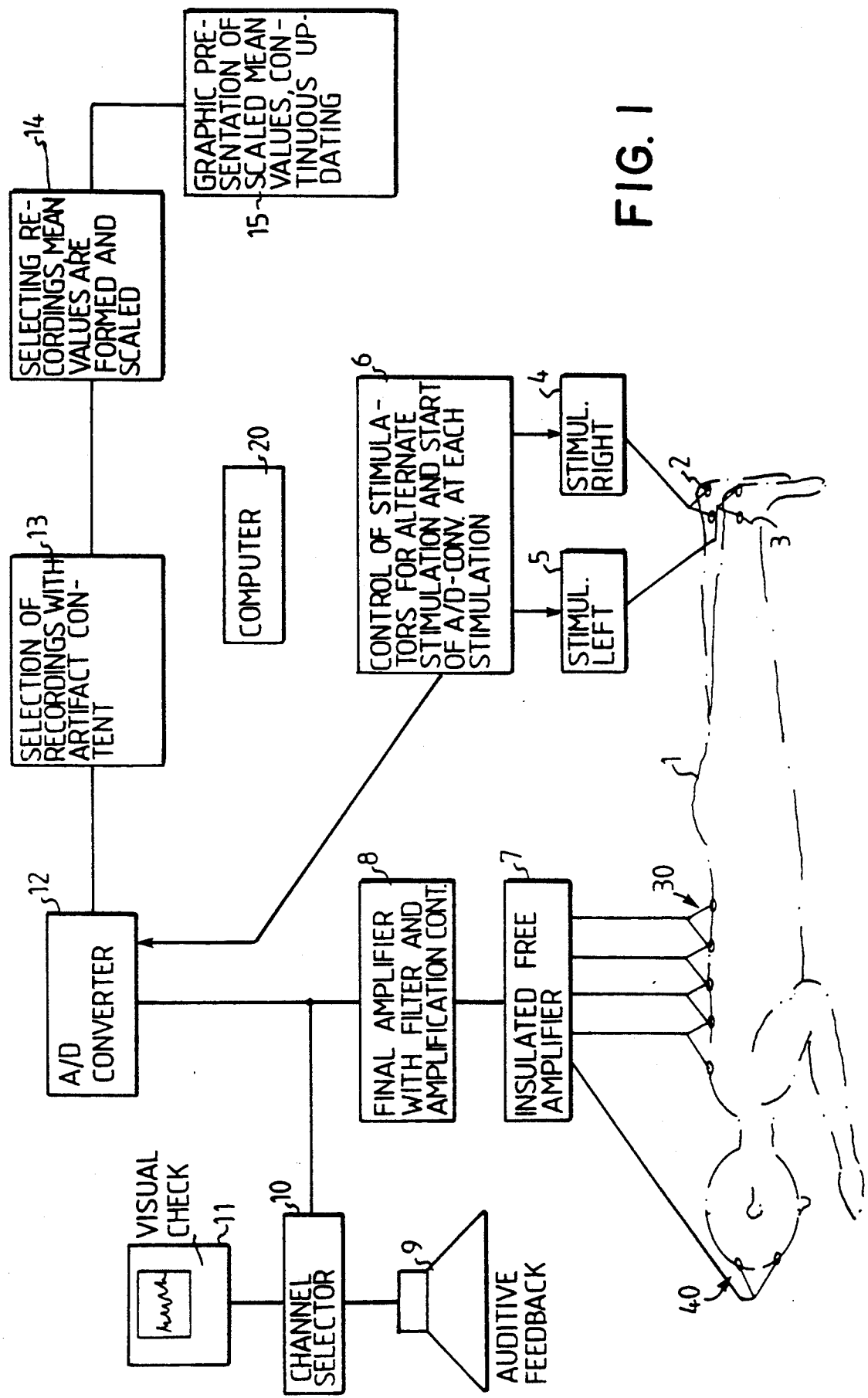
FIG. 1 illustrates schematically an inventive apparatus connected to a patient.

FIG. 1 is a block schematic which illustrates the principal construction of the exemplifying inventive apparatus. Some of the blocks shown denote functions which are carried out in a computer 20, and consequently the Figure shall be read partially as a flowsheet.

A patient 1 lies flat on his stomach on a bed or like support surface, as comfortably as possible. Pairs of electrodes 2, 3 are attached conductively to the skin on the patient's heels. Similar electrodes are attached at 30 along the patient's spine and at 40 on the crown of the patient's head.

Connected to the electrodes 2, 3 are electric stimulators 4, 5, which may be of a conventional kind capable of delivering voltage pulses that can be adjusted between 100-200V with durations of 0.1-0.5 ms, or current pulses of 0-40 mA of the same durations. The stimulators are controlled by the computer 20 so as to deliver stimulation pulses at a pulse rate of 2-5 Hz. There are produced in this way nerve signals which pass up through the legs, into the nerve paths of the spinal cord and up to the cortex. When arriving at respective locations along the spine, small potential variations in the skin occur, which can be detected successively via respective electrodes 30 and finally from the cortex through the electrodes 40. The electrodes 30 and 40 are connected, via earth screened conductor pairs, to an insulated preamplifier 7 and a following final amplifier 8 with filters and variable amplification which is either adjusted manually or adjusted to suitable amplification levels by means of the computer, so as to obtain a range suitable for receipt by a multiplex-operating A/D-converter. This converter may be a conventional 12-bit converter capable of detecting in time-multiplex all of the amplified signals, each having a sampling frequency of 2 kHz. Sampling begins at each stimulator pulse and has a duration of 100 ms, so as to obtain for each "simultaneously" measured electrode a time-series of 200 values per shot.

FIG. 1 also illustrates schematically the manner in which one of the signals arriving from the final amplifiers can be selected with the aid of an adjustable channel selector 10. This selected signal can be observed with the aid of a conventional oscilloscope 11 and passed to a loudspeaker 9, so that the patient is able to hear his own signals. Since muscle activations result in disturbances which dominate over the nerve signals, it is possible, by auditive feedback, to induce a concentrated patient to reduce this muscle activity, despite the fact that this muscle activity is not fully conscious or subjectively will-controlled. This is a surprisingly effective mechanism which contributes greatly to the good effect achieved by the present invention.

The output signals from the final amplifier 8 are passed to the A/D-converter where said signals are sampled. The sampled signals are selected with the aid of the computer 20, here drawn in the form of a box 13 and the mean values of the signals are formed in the box 14, and the results are successively displayed graphically on a screen 15. The boxes 6, 12, 13, 14 and 15 actually denote operations carried out by the computer, and consequently FIG. 1 should be seen partially as a flowsheet explaining the connection between the electrodes affixed to the patient and the measuring processes carried out.

The recorded measurements are processed in the following manner, in accordance with a computer program:

(1) Those series which present at least one value for which the A/D-converter has become saturated ("all ones") are rejected.

(2) In order to obtain a first characteristic quality factor, or merit factor, there is calculated for respective series the sum of the absolute values of the differences between pairs of adjacent values, e.g. values having a mutual order difference of 4:

$$A = \Sigma |X_i - X_{i-4}| \quad 4 \leq i \leq 200$$

(3) In order to obtain a second characteristic quality factor, there is calculated in the same way the sum of the differences between pairs which lie at a greater distance apart, e.g. 40 units:

$$B = \Sigma |X_i - X_{i-40}| \quad 40 \leq i \leq 200$$

(4) In order to obtain a third characteristic quality factor, there is first calculated the maximum difference between two values separated by 4 samplings:

$$C = max|X_i - X_{i-4}| \quad 4 \leq i \leq 200$$

In a first stage, 100 such series are recorded, for instance for each measuring signal which has not been rejected in accordance with (1) above. Thus, 100 value triads are obtained for these series. These can be seen as a shower of points in three-dimensional space laid in a space quadrant. These value triads are used to calculate a final criterion consisting of three numbers, such that, e.g., 25% of the 100 value triads satisfy this final criterion. For example, it is possible to calculate the mean value of each quality factor and to calculate the percentage thereof required for said rejection to be set to 25%

The actual measuring series begins when the first 100 series have been recorded and the triads stored. For each new measurement series of 200 values, the value triads are calculated and compared with the final criterion. If this criterion is satisfied by all three values, each of the 200 values is stored in its respective memory. Thus, successive accepted values are added together and ultimately there are obtained 200 mean values which when plotted form a curve which becomes progressively better and free from noise.

At the same time, the new value triad is recorded, while the first recorded value triad is discarded and a new final criterion is calculated. Thus, the final criterion is calculated in accordance with what can be called a iterative process which is adapted to prevailing conditions.

FIG. 1 illustrates these operations schematically in the box 13, where selection and triad storage takes place, whereas the accepted series are stored during successive formation of mean values in the box 14. The mean values of the curves can then be viewed successively on a screen in the box 15, and when the curves are considered satisfactory, the measuring process can be interrupted and the result printed out. Thus, curves are obtained from several locations along the path travelled by the nerve signal to the cortex.

The following procedure is taken for eliminating noise and artifacts:

a) Slow variations are already eliminated in the final amplifier 8, through a high pass filter, e.g. a RC-filter having a limit frequency of 0.5 Hz.

b) When the A/D-converter bottoms, the whole of the series being recorded at that time is rejected.

c) Series having an excessively high frequency content are eliminated by the quality factor A.

d) Series having excessive slow variations are eliminated by the quality factor B.

e) Series with a large number of pronounced variations are eliminated by the quality factor C.

These rejection criteria can be varied in many ways. What is essential is that each individual value array is subjected to variation criteria and either accepted or rejected as a whole, whereas the accepted values are summated point by point to obtain the mean values.

With regard to the aforesaid adaptive, auditive feedback, this is effected by passing one of the signals most subjected to muscle disturbances, thus a signal obtained from a pair of the electrodes 30, suitably amplified, to a loudspeaker 9, through a channel selector 10. The same signal can also be sent to an oscilloscope 11, for visual monitoring purposes. In certain cases, instead of using a loudspeaker, it may be more appropriate to use headphones worn by the patient. In the case of deaf people, it is suitable to position the oscilloscope 11 so that it can be seen by the patient. It has been found that, in general, the patient is able to lie still over at least prolonged periods, so as to practically eliminate muscle disturbances as a disturbance source, especially in combination with the aforesaid disturbance elimination.

Figure 2:
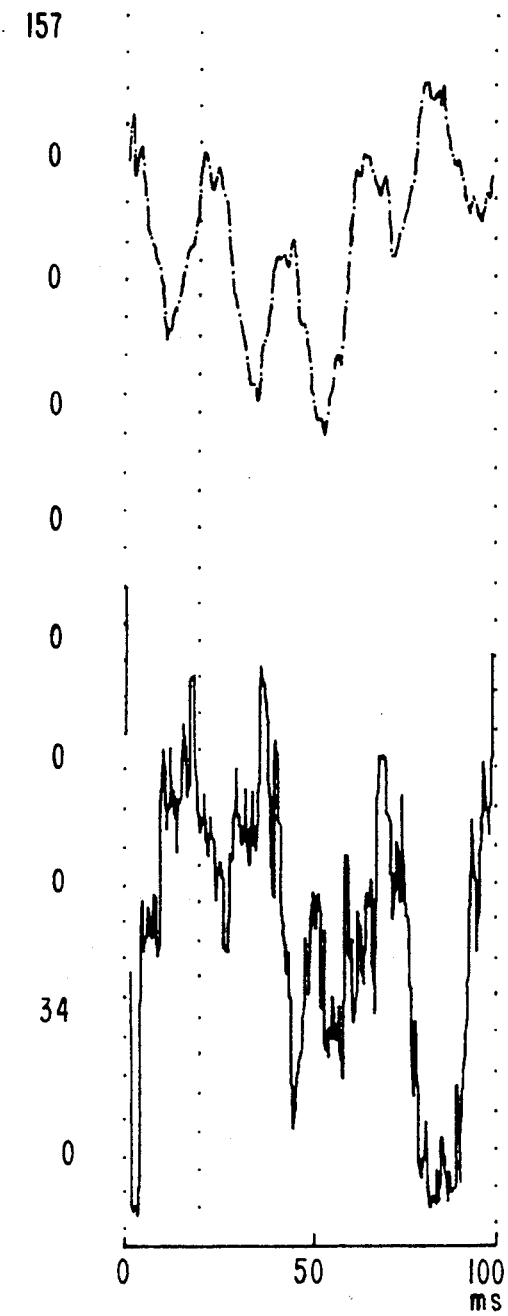
FIG. 2 illustrates a single recording of the nerve reaction as detected on the spine and on the crown of the patient over a period of 100 ms subsequent to administering a stimulating pulse.

FIG. 2 illustrates curves which are representative of single recordings from one single stimulant, the upper curve being the curved obtained through the electrodes attached to the crown of the patient's head and the lower curve being the curve obtained with the electrodes attached to the patient's spine. Particular note should be paid to the mains disturbance of 50 Hz shown in the upper curve. The lower curve is greatly disturbed.

Figure 3:
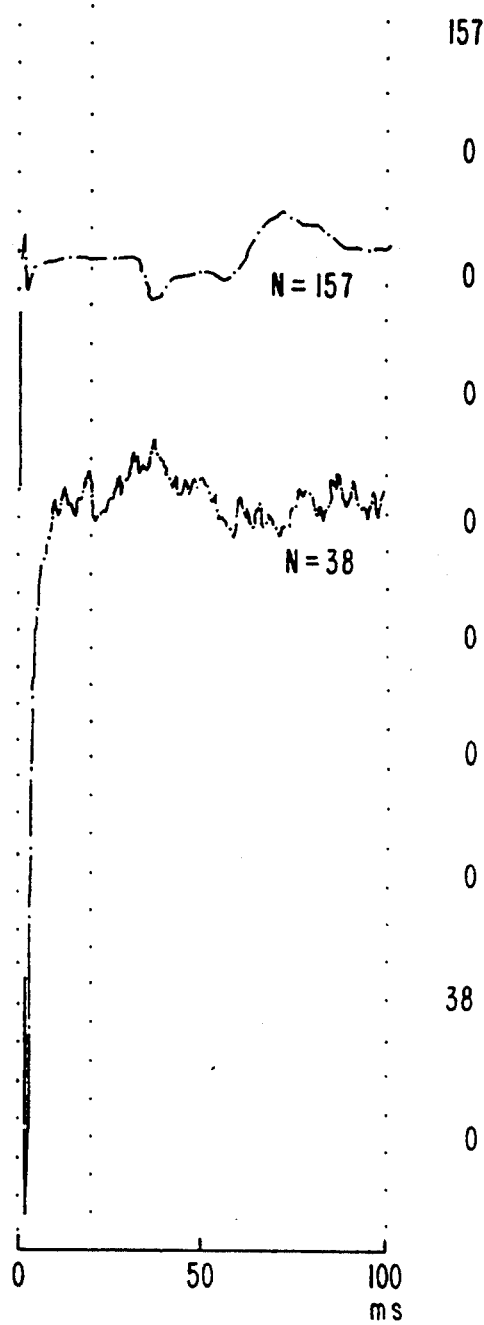
FIG. 3 illustrates mean value curves recorded at the same points as in FIG. 1, although subsequent to establishing the mean value of 157 and 38 accepted recordings respectively.

FIG. 3 illustrates an early result obtained when practicing the invention. The upper curve shows a mean value obtained when the crown electrodes and the lower curve shows a mean value for the spine electrodes. In the former case, the curve indicates the mean value of 157 individual recordings, whereas the lower curve indicates the mean value of only 38 recordings made during the same time period. Thus, as would be expected, the rejection is much greater in the case of the spine signals, where the artifact frequency is high.

Figure 4:
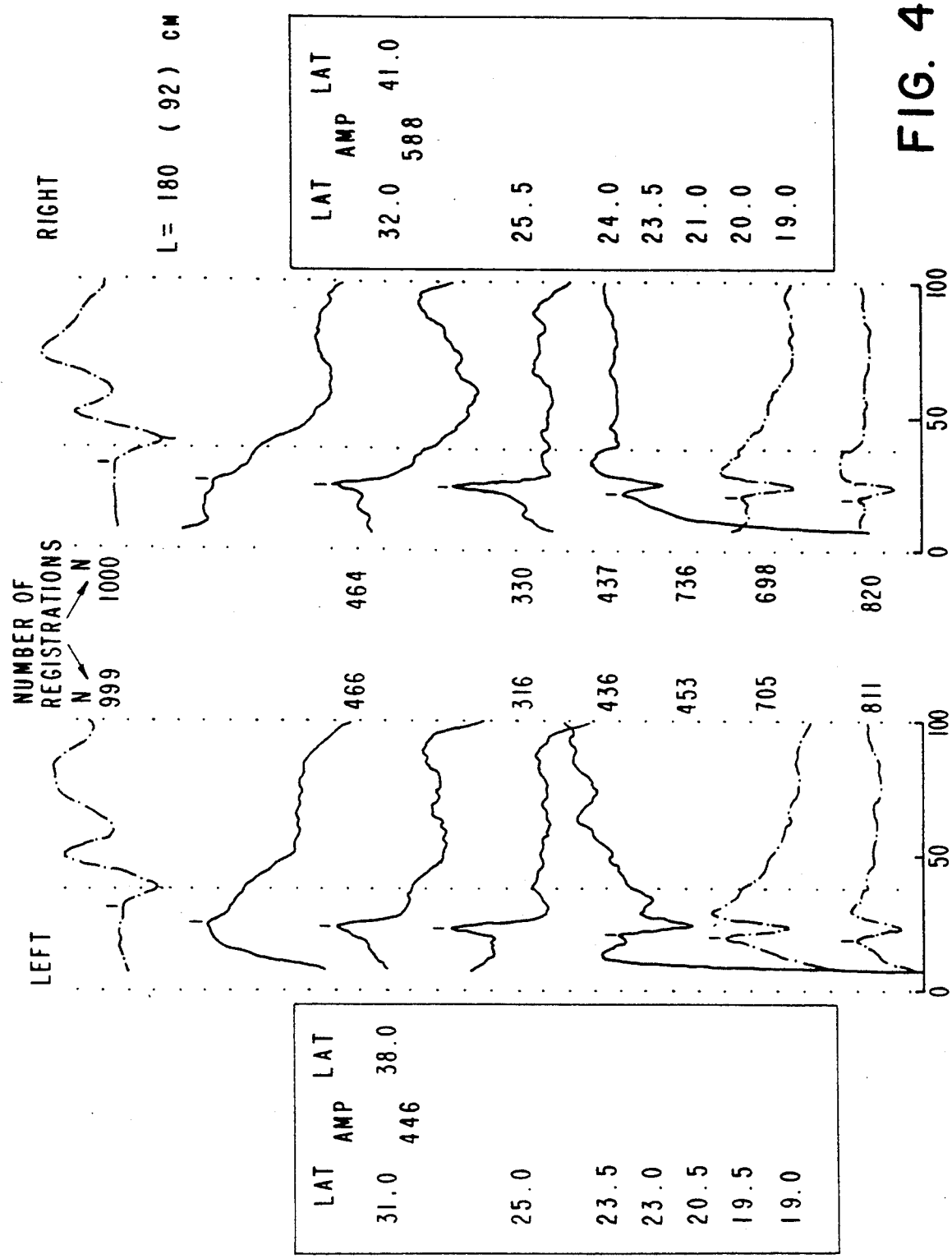
FIG. 4 illustrates the results obtained with complete measurement of the left side and the right side of a patient, recorded over a time of 15 minutes.

FIG. 4 shows an example of an end result obtained when stimulating the right and the left legs of a male adult aged 20 years and having a height of 180 cm. In addition to crown electrodes, the uppermost curves, signals have been recorded from six different pairs of electrodes distributed along the patient's spine. The so-called latency, i.e. the time lapse from the time of stimulation to the time of receiving the signal has been measured primarily with respect to signal maximum, although with regard to the cortex also the more conventional minimum-based signal. The conventionally defined latency of 38 ms for the left side of the patient is normal for a person of that height, whereas the latency on the right side of the patient, 41 ms, shows an abnormal asymmetry. In accordance with the invention, other information is obtained in addition to the information gained from this result. It is seen that the latencies of the spine signals for each pair on mutually opposite sides are similar, and consequently it is possible to exclude nerve damage downstream of these positions.

It is also of interest to note from a mathematical aspect that of all the thousands of curves accepted for the cortex in some cases less than one-third have been found acceptable in the upper part of the spine, whereas the conditions are improved closer to the end of the spine. It will also be noted that it has been possible to record this set of curves in less than fifteen minutes.

We claim:

1. An apparatus for measuring the transport time of nerve signals of a patient, said apparatus comprising:
   (a) a plurality of stimulating electrodes capable of transmitting an electrical signal to the patient;
   (b) a plurality of detecting electrode-pairs adapted for attachment to the patient's skin;
   (c) amplifying means connected to said electrode-pairs capable of amplifying the electrical signals detected by said electrode-pairs;
   (d) an A/D-converter capable of receiving the amplified electrical signals generated by said amplifying means;
   (e) a computer capable of processing the amplified electrical signals received by said A/D-converter and storing said signals as numerical sequences at specific time points;
   (f) means for excluding select numerical sequences;
   (g) means for summating the numbers in the numerical sequences that are not excluded in step (f);
   (h) means for determining the mean values for said summated numbers; and
   (i) means for signalling the output signals of said amplifying means to the patient's consciousness.

2. The apparatus according to claim 1 wherein said means for signalling to the patient's consciousness comprises a sound generator.

3. The apparatus according to claim 2 wherein said sound generator is a loudspeaker or headphones.

4. The apparatus according to claim 1 wherein said means for signalling to the patient's consciousness comprises an image generator.

5. The apparatus according to claim 4 wherein said image generator is an oscilloscope.

6. The apparatus according to claim 1 wherein said electrode-pairs comprise an electrode-pair adapted for attachment to the crown of the patient's head, and from 4 to 9 electrodes adapted for attachment along the patient's spine.

7. The apparatus according to claim 1 wherein the signals that are transmitted by said stimulating electrodes are stored and recorded separately.

8. A method of measuring the transport time of nerve impulses as the nerve impulses travel from an extremity of a patient to the cortex of said patient, said method comprising:
   (a) attaching a plurality of stimulating electrodes capable of transmitting an electrical signal to said patient;
   (b) attaching a plurality of detecting electrode-pairs to said patient;
   (c) amplifying the electrical signals detected by said electrode-pairs;
   (d) transmitting the amplified electrical signals of (c) to an A/D-converter;
   (e) processing and storing the amplified electrical signals received by said A/D converter in a computer as numerical sequences at specific time points;
   (f) excluding select numerical sequences;
   (g) summating the numbers in the remaining numerical sequences;
   (h) determining the mean values of said summated numbers;
   (i) signalling the amplified signals to said patient.

9. The method according to claim 8 wherein said stimulating electrodes are attached to said patient's extremities.

10. The method according to claim 8 wherein said detecting electrode-pairs are attached to said patient's cortex.

11. The method according to claim 8 wherein said detecting electrode-pairs are attached to said patient's spine.

12. The method according to claim 11 wherein said detecting electrode-pairs are attached at nine or more different locations on said patient's spine.

13. The method according to claim 8 wherein said amplified signals are signalled to said patient audibly, visually or a combination thereof.

14. A method of comparing the nerve impulses generated by the left side of a patient with the nerve impulses generated by the right side of a patient, said method comprising:
 (a) attaching a plurality of stimulating electrodes capable of transmitting an electrical signal to the left side of said patient;
 (b) attaching a plurality of stimulating electrodes capable of transmitting an electrical signal to the right side of said patient;
 (c) attaching a plurality of detecting electrode-pairs to said patient;
 (d) alternately activating the stimulating electrodes so that while one side of said patient is being stimulated the opposite side of said patient is not being stimulated;
 (e) amplifying the electrical signals detected by said electrode-pairs;
 (f) transmitting the amplified electrical signals of (e) to an A/D-converter;
 (g) processing and storing the amplified electrical signals received by said A/D-converter in a computer as numerical sequences at specific time points;
 (h) excluding select numerical sequences;
 (i) summating the numbers in the remaining numerical sequences;
 (j) signalling the amplified signals to said patient.

15. The method according to claim 14 wherein the electrical signals generated by the right side of said patient are stored and processed separately from the electrical signals generated by the left side of said patient.

16. The method according to claim 14 wherein said stimulating electrodes are attached to said patient's extremities.

17. The method according to claim 14 wherein said detecting electrode-pairs are attached to said patient's cortex.

18. The method according to claim 14 wherein said detecting electrode-pairs are attached to said patient's spine.

19. The method according to claim 18 wherein said detecting electrode-pairs are attached to said patient's spine at nine or more different locations.

20. The method according to claim 14 wherein said amplified signals are signalled to said patient audibly, visually, or a combination thereof.

* * * * *